(12) United States Patent
Lee et al.

(10) Patent No.: US 8,505,354 B2
(45) Date of Patent: Aug. 13, 2013

(54) COMPENSATED GAS DETECTORS

(75) Inventors: JaeJin Lee, Seoul (KR); JuWan Park, Seongnam-si (KR); JoungHo Lim, Guro-gu (KR)

(73) Assignee: Life Safety Distribution AG, Hegnau (CH)

(*) Notice: Subject to any disclaimer, the term of this patent is extended or adjusted under 35 U.S.C. 154(b) by 55 days.

(21) Appl. No.: 13/161,561

(22) Filed: Jun. 16, 2011

(65) Prior Publication Data

US 2012/0318037 A1 Dec. 20, 2012

(51) Int. Cl.
*G01N 27/04* (2006.01)

(52) U.S. Cl.
USPC .......................................................... 73/1.07

(58) Field of Classification Search
None
See application file for complete search history.

(56) References Cited

U.S. PATENT DOCUMENTS 6,742,382 B2 * 6/2004 Warburton et al. .......... 73/23.31

* cited by examiner

*Primary Examiner* — Robert R Raevis
(74) *Attorney, Agent, or Firm* — Husch Blackwell LLP

(57) ABSTRACT

A compensated gas detector incorporates first and second pellistors combined with first and second resistors and an intervening switch. Control circuits can close the switch for normal gas detection. The switch can be opened to carry out diagnostic measurements. A compensation coefficient can be established in order to compensate outs from the pellistors due to mechanical damage thereto.

6 Claims, 5 Drawing Sheets

COMPENSATED GAS DETECTORS

FIELD

The application pertains to gas detectors which incorporate catalytic bead sensors. More particularly, detectors which can compensate outputs from such sensors in response to mechanical damage to the beads, or their mounting structures.

BACKGROUND

Gas detectors which incorporate catalytic bead sensors are widely used to measure combustible gas. Such sensors can be incorporated into a Wheatstone bridge with one sensor providing a sensing function and a second acting as a reference. However, while useful, such circuit configurations are sensitive to mechanical impact. This is especially the case when bead sensors are incorporated into portable gas detectors. When a user drops a detector, the electro/mechanical structure of the Wheatstone bridge can be broken. Outputs from the bridge can be floating even without a gas reaction. This can be a problem when working in an explosive atmosphere.

FIG. 1 illustrates aspects of electrical connections and mechanical arrangements of known multiple bead sensing units.

It has been known to use a relatively simple zero compensation technique with bead sensors to make zero gas readings without knowing the reason why the zero gas reading is floating. This process has limited compensation ability and it is undesirable, with explosive gases, to permit zeroing across a wide range.

DETAILED DESCRIPTION

Figure 1:
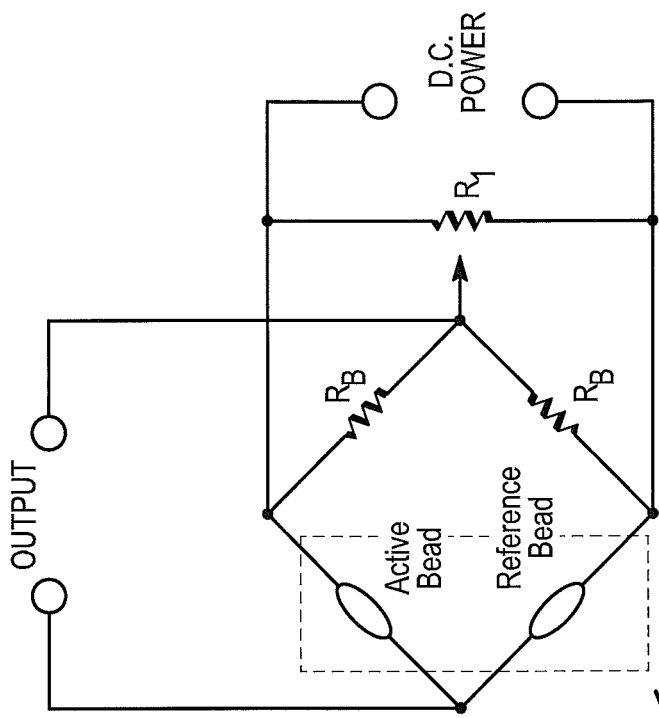
FIG. 1 illustrates a prior art sensor configuration.
Figure 1:
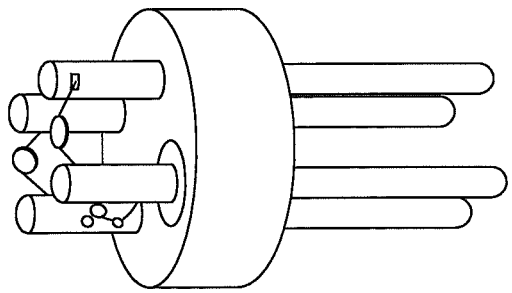

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In one aspect of the present embodiments, resistance values of a reference and an active, gas responsive, bead can be measured independently. The resistance of the active bead can be changed by both gas reactions and external impacts. The resistance of the reference bead is changed by external impacts or environmental reactions, for example poisoning and degradation of a reference bead.

The consequences of external impacts can be detected by determining if the value of the resistance of the reference bead has changed. By measuring the current which flows through the beads and the voltages across each bead, distorted sensor outputs, due to external impacts, can be detected and compensated.

In another aspect, detectors which incorporate catalytic bead sensors, and associated reference bead sensors, can in a diagnostic mode, verify the condition of the beads by evaluating reference bead resistance changes due to mechanical impact, or poisoning. If incorporated into a Wheatstone bridge-type of electrical structure, the beads can be switched between an operational state and a diagnostic state to determine bead resistance.

A present reference bead resistance value can be compared to a prior, pre-stored value to determine if a change has taken place. Where a resistance change indicative of a mechanical or electrical problem is present, the detector can carry out a compensation process. When compensated, the detector can continue to be used even in the presence of explosive gases.

Figure 2:
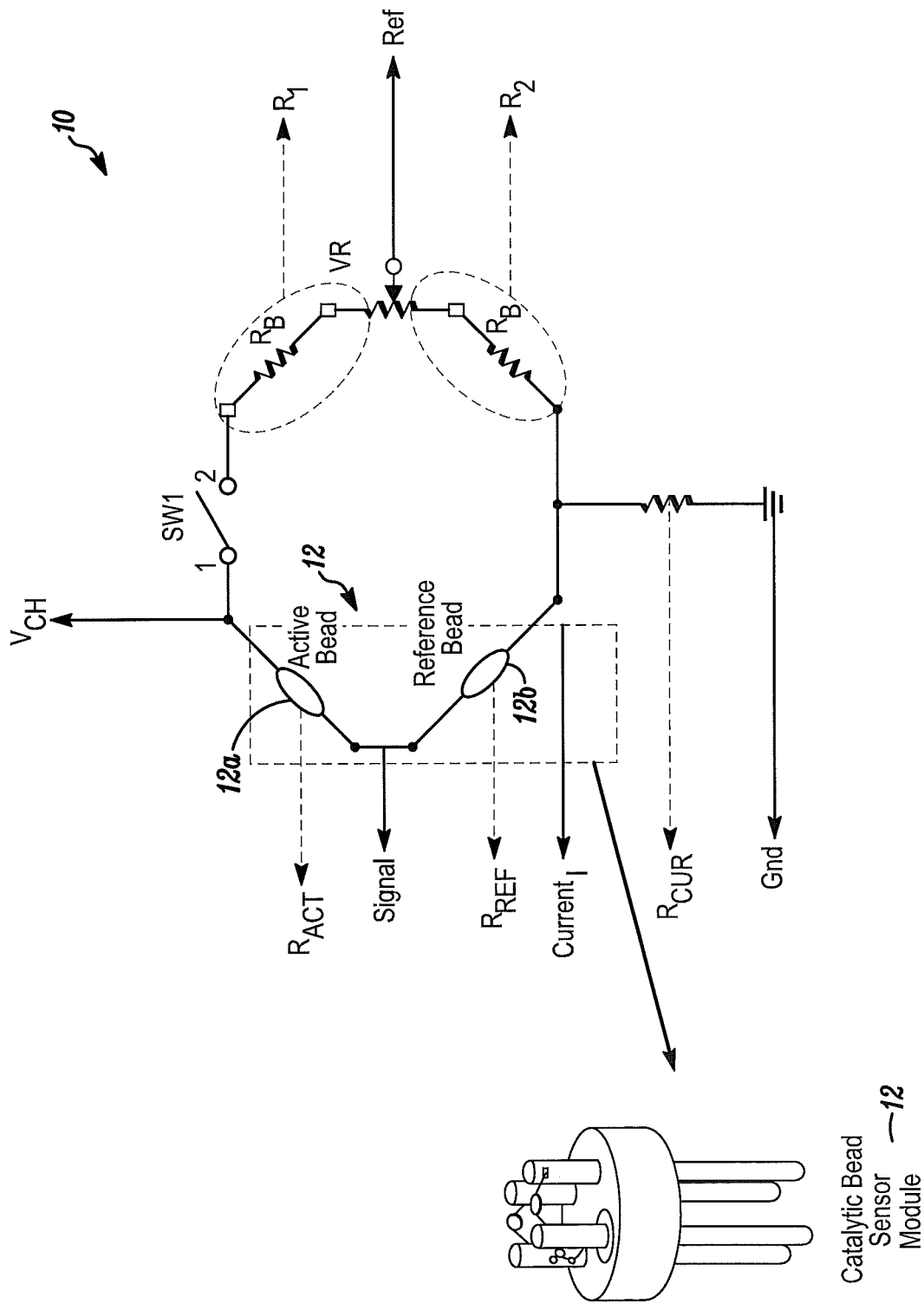
FIG. 2 is a diagram of a sensor configuration in accordance herewith.

FIG. 2 illustrates aspects of a compensatable, multi-state, multi-bead sensor/reference unit 10. Unit 10 incorporates a catalytic bead sensor module 12 which mechanically carries a gas responsive, active bead, pellistor, 12a and a reference bead, pellistor, 12b. A controllable switch SW1 is provided between active bead 12a and two additional fixed resistors R1, R2 which complete a bridge-type structure in combination with beads/resistors 12a,b when switch SW1 is closed. When switch SW1 is open, the branches 12a,b and R1, R2 can operate independently.

Switch SW1 is normally closed when unit 10 is measuring gas and is open, off, when checking bead resistance. When SW1 is open, off, the voltage Vch is divided by the resistance of bead 12a, the resistance of bead 12b and a resistance Rcur to ground. In this state, sensor current I can be calculated using the voltage across Rcur, which can be expected to have a value on the order of one ohm. The resistance value of the reference bead 12b and the active bead 12a can be calculated by measuring the voltage across the beads and dividing by sensor current I.

Figure 3:
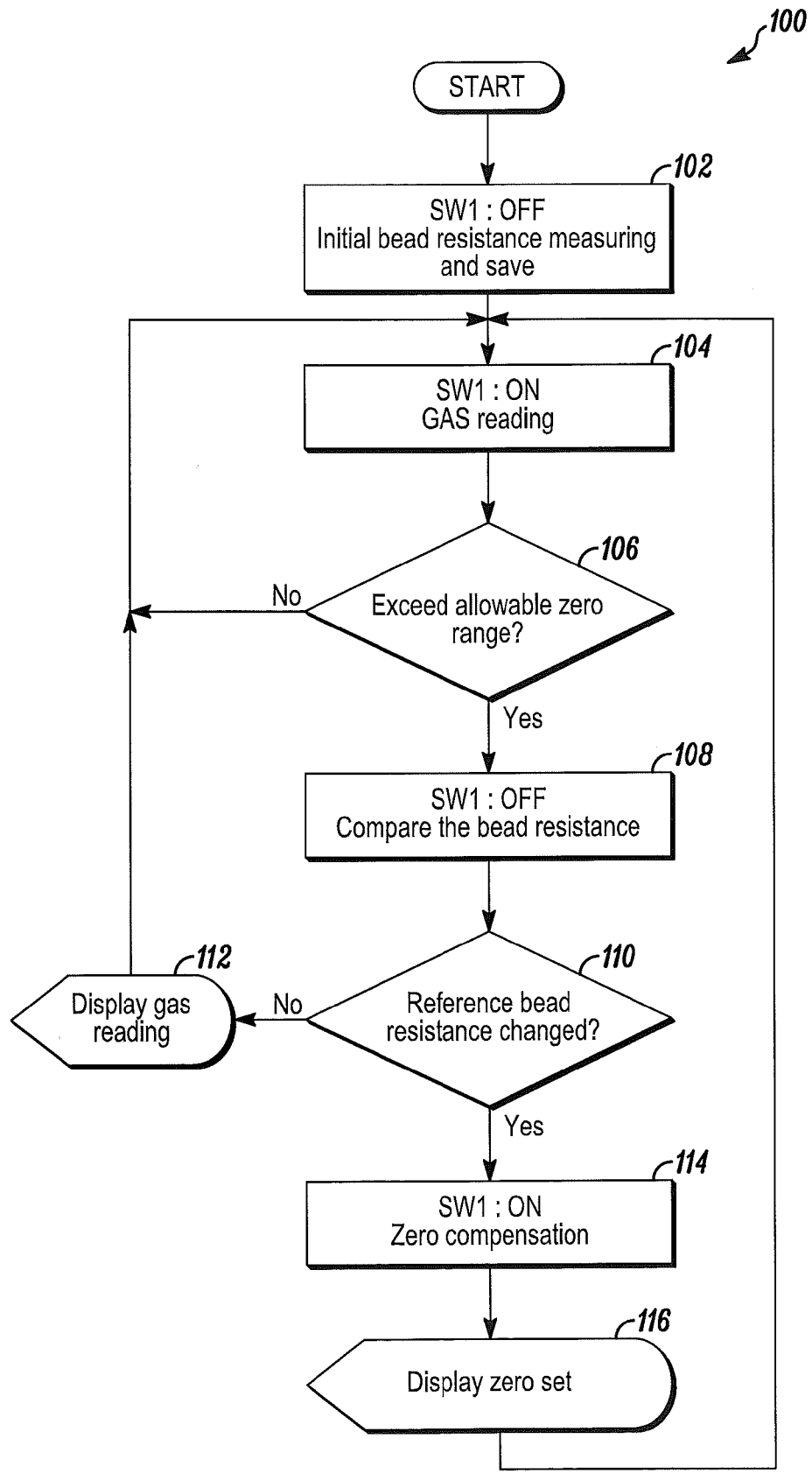
FIG. 3 is a flow diagram illustrating a method of operating the sensor configuration of FIG. 2.

FIG. 3 illustrates aspects of a method 100 of operating a detector 10-1, best seen in FIG. 4, discussed below. With SW1 open, off, initial bead resistance determination can be carried out and the associated values saved, stored, as at 102. Switch SW1 can then be closed, turned on, to read the ambient gas concentration as at 104.

A determination can be made, as at 106, as to whether an allowable zero gas concentration range has been exceeded. If not, gas concentration reading continues, as at 104. Otherwise, as at 108, switch SW1 is opened, off, and current bead resistance is compared to one or more previously determined and stored bead resistance values. At 110 a determination is made as to whether reference bead resistance has changed, if not, a gas concentration can be displayed, as at 112. If a resistance change has been detected, switch SW1 is closed, on, and a compensation process is carried out. IA zero concentration setting can be displayed as at 116.

Figure 4:
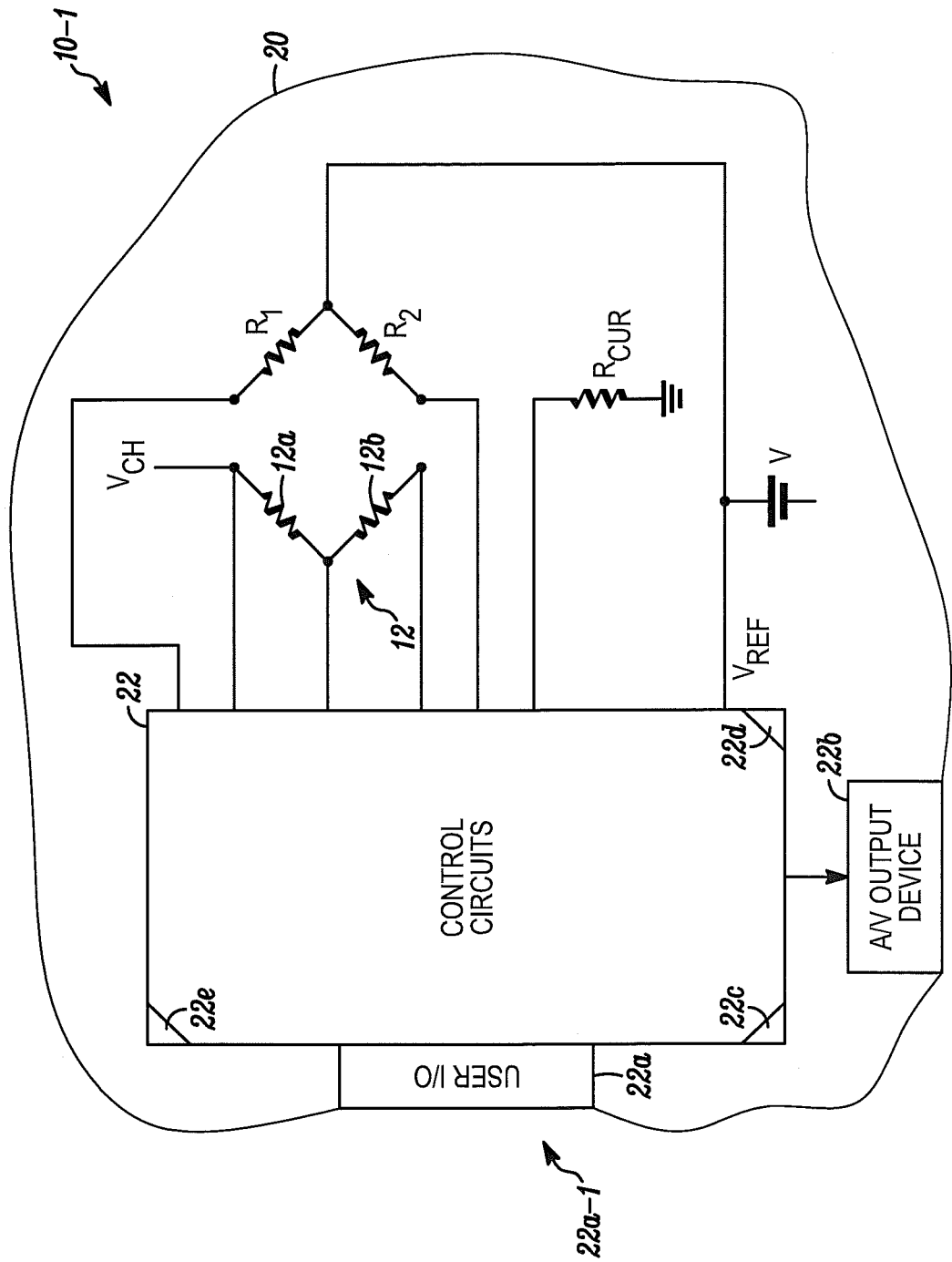
FIG. 4 is a diagram of a gas detector in accordance herewith.

FIG. 4 illustrates a detector 10-1 in accordance herewith. Previously discussed elements have been assigned the same identification numerals as above, and need not be discussed further.

Detector 10-1 can include a portable housing 20, which might be attachable to clothing of a user. Detector 10-1 can be energized by a self-contained battery V as would be understood by those of skill in the art. The housing 20 can also carry control circuits 22.

Control circuits 22 can include a user I/O port 22a, which might include manually operable inputs and one or more outputs, for example a two dimensional numeric gas concentration display 22a-1. Control circuits 22 can also be coupled to an audio/visual alarm indicating output device 22b, also carried by housing 20.

Control circuits 22 can include a switch, such as SW1, implemented as a semiconductor switch in turn coupled into the beads 12a, b (module 12), and resistors R1, R2 as well as Rcur to implement the method 100 discussed previously. Control circuits can, at least in part, be implemented with a programmable processor 22c, and pre-stored control software 22d. A data storage unit 22e can be used to store resistance values for the beads 12a,b measured on an on-going basis to implement the process 100 of FIG. 3 or variations thereof without limitation.

Figure 5A:
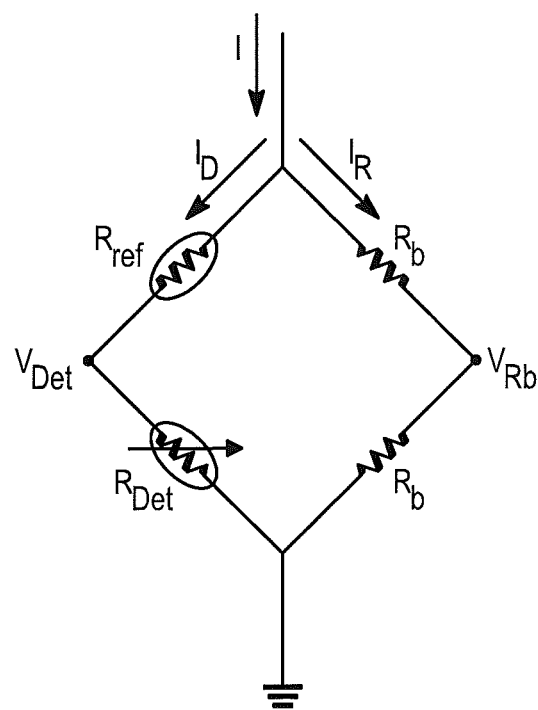
FIGS. 5A, 5B illustrate aspects of a compensating methodology.

FIGS. 5A, B illustrate aspects of measurements and resistance determinations in establishing a compensation parameter, at a particular time, to be used by control circuits 22 in determining compensated concentration values which take into account resistance impact caused changes in the resistance value of reference bead 12b.

With reference to FIG. 5A, gas concentration C, prior to any impact, can be determined by making the following measurements:

$$I_D = \frac{2R_b}{R_{ref} + R_{Det} + 2R_b} I \quad I_R = \frac{R_{ref} + R_{Det}}{R_{ref} + R_{Det} + 2R_b} I$$

$$V_{R_{Det}} = \frac{2R_b R_{Det}}{R_{ref} + R_{Det} + 2R_b} I \quad V_{R_b} = \frac{(R_{ref} + R_{Det})R_b}{R_{ref} + R_{Det} + 2R_b} I$$

After having made the above measurements, gas concentration can be established by:

$$C = V_{R_b} - V_{RDet} = \frac{(R_{ref} - R_{Det})R_b}{R_{ref} + R_{Det} + 2R_b} I$$

Figure 5B:
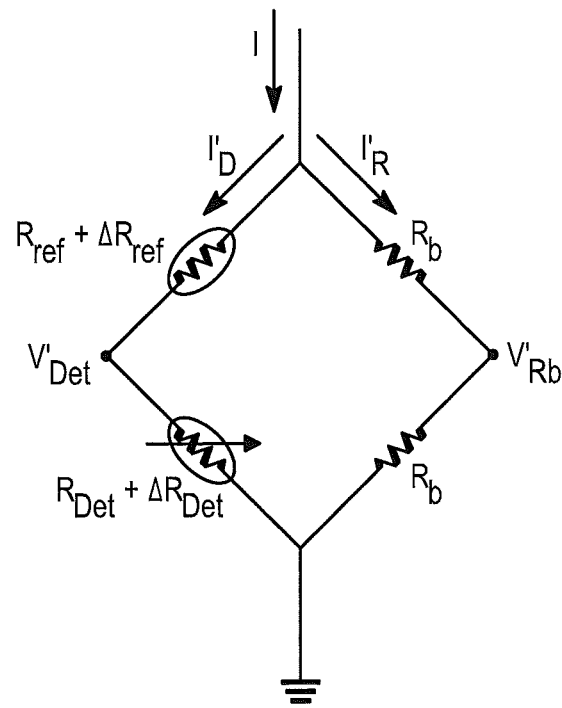

With reference to FIG. 5B, a measured value of concentration C', after impact can be determined as follows:

$$I'_D = \frac{2R_b}{R_{ref} + R_{Det} + 2R_b + \Delta R_{ref} + \Delta R_{Det}} I$$

$$I'_R = \frac{R_{ref} + R_{Det} + \Delta R_{ref} + \Delta R_{Det}}{R_{ref} + R_{Det} + 2R_b + \Delta R_{ref} + \Delta R_{Det}} I$$

$$V'_{R_{Det}} = \frac{2R_b R_{Det} + 2R_b \Delta R_{Det}}{R_{ref} + R_{Det} + 2R_b + \Delta R_{ref} + \Delta R_{Det}} I$$

$$V'_{R_b} = \frac{(R_{ref} + R_{Det} + \Delta R_{ref} + \Delta R_{Det})R_b}{R_{ref} + R_{Det} + 2R_b + \Delta R_{ref} + \Delta R_{Det}} I$$

Having made the above measurements, concentration after impact, C', can be established by:

$$C' = V'_{R_b} - V'_{RDet} = \frac{(R_{ref} + \Delta R_{ref} - R_{Det} - \Delta R_{Det})R_b}{R_{ref} + R_{Det} + 2R_b + \Delta R_{ref} + \Delta R_{Det}} I$$

A compensation parameter can be determined by:

$$\text{Compensation} = \frac{(R_{ref} + R_{Det} + 2R_b)R_b(\Delta R_{ref} - \Delta R_{Det}) - (R_{ref} - R_{Det})R_b(\Delta R_{ref} + \Delta R_{Det})}{(R_{ref} + R_{Det} + 2R_b)(R_{ref} + R_{Det} + 2R_b + \Delta R_{ref} + \Delta R_{Det})}$$

Compensated concentration C then corresponds to:

$$C = C' - \frac{(R_{ref} + R_{Det} + 2R_b)R_b(\Delta R_{ref} - \Delta R_{Det}) - (R_{ref} - R_{Det})R_b(\Delta R_{ref} + \Delta R_{Det})}{(R_{ref} + R_{Det} + 2R_b)(R_{ref} + R_{Det} + 2R_b + \Delta R_{ref} + \Delta R_{Det})} I$$

The following illustrate exemplary values of parameters when the unit 10 is in different operational states. In Example 1, initial values of catalytic bead resistance are measured with SW1 open, off, in a diagnostic state:

| | |
|---|---|
| Vdet (V) | 1.3661 |
| Vdet + Vref (V) | 2.7339 |
| Vref (V) | 1.3678 |
| Vrsense (V) | 0.2 |
| Rref (ohm) | 6.839 |
| Rdet (ohm) | 6.8305 |
| Output/1% LEL (V) | 0.000925 |
| Rb (ohm) | 2000 |
| Δrdet (ohm) | 0 |
| Δrref (ohm) | 0 |
| Zero Compensation Factor | −0.9157893 |
| Gas reading (% LEL) | 0 |

EXAMPLE 1

The initial values Rref, and Rdet, both in ohms, can be stored in storage unit 22e.

In Example 2, gas concentration can be measured without an alteration of resistance value of the reference bead 12b. The measured values of Rref and Rdet are compared with previously stored values thereof. If Rref is substantially the same, unchanged, then gas concentration C can be determined, with SW1 closed, on, in the measuring mode.

| | |
|---|---|
| Vdet (V) | 1.3851 |
| Vdet + Vref (V) | 2.7529 |
| Vref (V) | 1.3678 |
| Vrsense (V) | 0.2 |
| Rref (ohm) | 6.839 |
| Rdet (ohm) | 6.9255 |
| Output/1% LEL (V) | 0.000925 |
| Rb (ohm) | 2000 |
| Δrdet (ohm) | 0.095 |
| Δrref (ohm) | 0 |
| Raw Gas value | 9.3192825 |
| Gas reading (% LEL) | 10.235072 |

EXAMPLE 2

In Example 3, changes to the value of the resistance of reference bead 12b are measured and the compensation parameter is determined. In this regard, with SW1 open, off, in the diagnostic mode, the measured values of Rref and Rdet are compared with pre-stored values. If Rref has changed, a value of the change in Reref is determined. The new Rref value is then stored in the storage unit 22e.

| | |
|---|---|
| Vdet (V) | 1.3661 |
| Vdet + Vref (V) | 2.7471 |
| Vref (V) | 1.381 |
| Vrsense (V) | 0.2 |
| Rref (ohm) | 6.905 |
| Rdet (ohm) | 6.8305 |

-continued

| | |
|---|---|
| Output/1% LEL (V) | 0.000925 |
| Rb (ohm) | 2000 |
| Δrdet (ohm) | 0 |
| Δrref (ohm) | 0.066 |
| Zero Compensation Factor | −8.0264921 |
| Gas reading (% LEL) | 0 |

EXAMPLE 3

In Example 4, gas concentration is measured with reference to an updated, changed value of resistance of the reference bead 12b. In this regard, the measured values of Rref, Rdet with SW1 closed, on, in the measuring mode are compared with the latest values or data stored in unit 22e. If the value of Rref has not changed, gas concentration C can be determined with the following results.

| | |
|---|---|
| Vdet (V) | 1.3783 |
| Vdet + Vref (V) | 2.7593 |
| Vref (V) | 1.381 |
| Vrsense (V) | 0.2 |
| Rref (ohm) | 6.905 |
| Rdet (ohm) | 6.8915 |
| Output/1% LEL (V) | 0.000925 |
| Rb (ohm) | 2000 |
| Δrdet (ohm) | 0.095 |
| Δrref (ohm) | 0.066 |
| Raw Gas value | 2.2085798 |
| Gas reading (% LEL) | 10.235072 |

EXAMPLE 4

In summary, changes in the values of the resistance of the reference bead 12b of a gas detector can be determined. In a diagnostic mode, the detector can measure and then establish catalytic bead resistance values. Abnormal gas concentration values, caused by reference bead resistance value changes due to mechanical impact, poisoning or reference bead degradation can be compensated so that the user can continue to carry and rely on output indicia from the detector.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A gas detector comprising:
   first and second pellistors, coupled in series;
   a controllable switch;
   first and second fixed resistors, coupled in series, wherein the pellisors are coupled to both the switch and to the resistors; and
   circuitry coupled to the switch, the pellistors and the resistors, wherein the circuitry places the switch into a conducting state to establish a gas concentration state and into an open circuit to establish a compensation state, wherein the circuitry independently measures respective resistance values of the first and second pellistors and stores measured resistance values on an on-going basis in a data storage unit and wherein the gas detector determines a concentration of the gas in the gas concentration state based upon resistance values of the first and second fixed resistors and the respective stored resistance values of the first and second pellistors.

2. A detector as in claim 1 which includes a storage unit coupled to the circuitry to store resistance values for at least one of the pellistors.

3. A detector as in claim 2 which includes circuitry to compare a current pellistor resistance value with a store resistance value.

4. A detector as in claim 3 where the circuitry determines a compensation coefficient in response to at least one stored resistance value.

5. A detector as in claim 1 where responsive to a pellistor resistance value, a compensated gas concentration is established by the circuitry.

6. A detector as in claim 5 which includes a housing which carries the pellistors, the switch, the resistors and the circuitry with the circuitry implenieted at least in part with a programmed processor.

* * * * *